United States Patent
Rogers et al.

[11] Patent Number: 5,803,079
[45] Date of Patent: *Sep. 8, 1998

[54] ENDOTRACHEAL TUBE POSITIONER

[75] Inventors: Russell L. Rogers, Munith; Gary B. Challender, Grass Lake, both of Mich.

[73] Assignee: Aeroquip Corporation, Maumee, Ohio

[*] Notice: The term of this patent shall not extend beyond the expiration date of Pat. No. 5,555,881.

[21] Appl. No.: 688,536

[22] Filed: Jul. 30, 1996

Related U.S. Application Data

[62] Division of Ser. No. 273,409, Jul. 11, 1994, Pat. No. 5,555,881.

[51] Int. Cl.$^6$ .......................... A61M 25/01; A61M 31/60
[52] U.S. Cl. .............................. 128/207.14; 128/200.26; 128/262.17; 128/911; 128/DIG. 26; 604/174; 604/179
[58] Field of Search ................... 128/200.26, 207.14, 128/207.17, 911, 912, DIG. 26; 604/174, 179

[56] References Cited

U.S. PATENT DOCUMENTS

| | | | |
|---|---|---|---|
| 3,760,811 | 9/1973 | Andrew | 128/207.17 |
| 3,906,592 | 9/1975 | Sakusegawa et al. | 24/543 |
| 4,223,671 | 9/1980 | Muta | 128/200.263 |
| 4,235,229 | 11/1980 | Ranford et al. | 128/207.17 |
| 4,249,529 | 2/1981 | Nestor et al. | 128/207.17 |
| 4,313,437 | 2/1982 | Martin | 128/207.17 |
| 4,326,515 | 4/1982 | Shaffer et al. | 128/207.17 |
| 4,351,331 | 9/1982 | Gereg | 128/207.17 |
| 4,378,012 | 3/1983 | Brown | 128/207.17 |
| 4,392,857 | 7/1983 | Beran | 604/179 |
| 4,445,527 | 5/1984 | Hinton | 128/207.17 |
| 4,483,337 | 11/1984 | Clair | 128/207.17 |
| 4,498,903 | 2/1985 | Mathew . | |
| 4,516,293 | 5/1985 | Beran | 24/16 PB |
| 4,520,813 | 6/1985 | Young | 128/207.17 |
| 4,530,354 | 7/1985 | Froilan | 128/207.17 |
| 4,537,192 | 8/1985 | Foster | 128/207.17 |
| 4,548,200 | 10/1985 | Wapner | 128/207.17 |
| 4,592,351 | 6/1986 | Smith et al. | 128/207.17 |
| 4,658,814 | 4/1987 | Anderson | 128/207.17 |
| 4,683,882 | 8/1987 | Laird | 128/207.17 |
| 4,744,358 | 5/1988 | McGinnis | 128/207.17 |
| 4,774,943 | 10/1988 | Yu | 128/207.17 |
| 4,774,944 | 10/1988 | Mischinski | 128/107.17 |
| 4,844,061 | 7/1989 | Carroll | 128/201 |
| 4,867,154 | 9/1989 | Potter | 128/207.17 |
| 5,009,227 | 4/1991 | Niewstad | 128/207.17 |
| 5,026,352 | 6/1991 | Anderson . | |
| 5,038,778 | 8/1991 | Lott | 128/207.17 |
| 5,042,477 | 8/1991 | Lewis | 128/207.17 |
| 5,069,206 | 12/1991 | Crosbie | 128/207.17 |
| 5,076,269 | 12/1991 | Austin | 128/207.17 |
| 5,123,410 | 6/1992 | Greene et al. | 128/207.17 |
| 5,226,892 | 7/1993 | Boswell . | |
| 5,237,988 | 8/1993 | McNeese | 128/207.17 |
| 5,295,480 | 3/1994 | Zemo | 24/543 |
| 5,320,097 | 6/1994 | Clemens et al. . | |
| 5,398,679 | 3/1995 | Freed . | |
| 5,490,504 | 2/1996 | Vrona et al. . | |

FOREIGN PATENT DOCUMENTS

| 2918810 | 10/1980 | Germany | 24/455 |
|---|---|---|---|

OTHER PUBLICATIONS

Sears Craftsman Tools, 1991/82 Catalog of Power and Hand Tools, p. 116.
Olympic Medical–Endo–Lok Brochure –2 pages.

*Primary Examiner*—Mickey Yu
*Assistant Examiner*—William J. Deane, Jr.
*Attorney, Agent, or Firm*—Emch, Schaffer, Schaub & Porcello Co., L.P.A.

[57] ABSTRACT

An endotracheal tube holder or positioner is disclosed having a collar member formed from at least two body portions engaged together to form a central orifice extending axially therethrough. The body portions are engaged together by a hinge member and a clasp. Each body portion includes a radially deflective clamping member, the clamping member forming an adjustable clamping orifice designed to accommodate and grip endotracheal tubes of varying diameters.

4 Claims, 4 Drawing Sheets

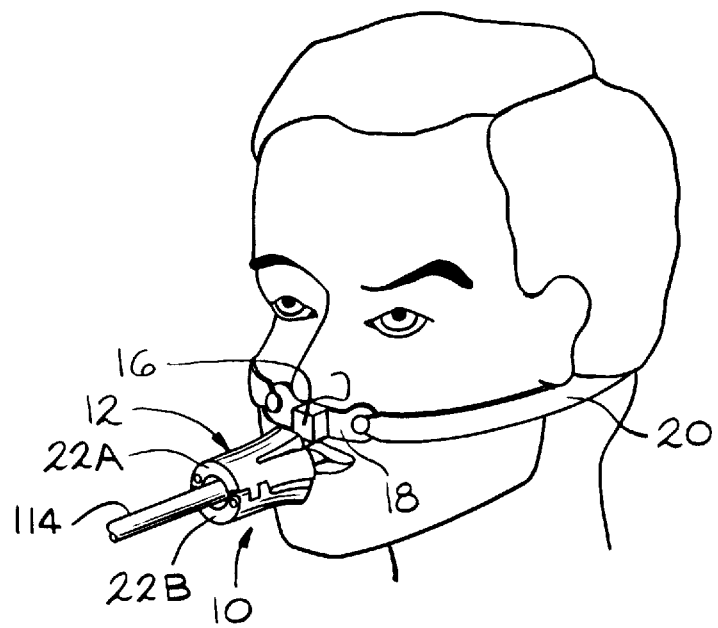
FIG. 1
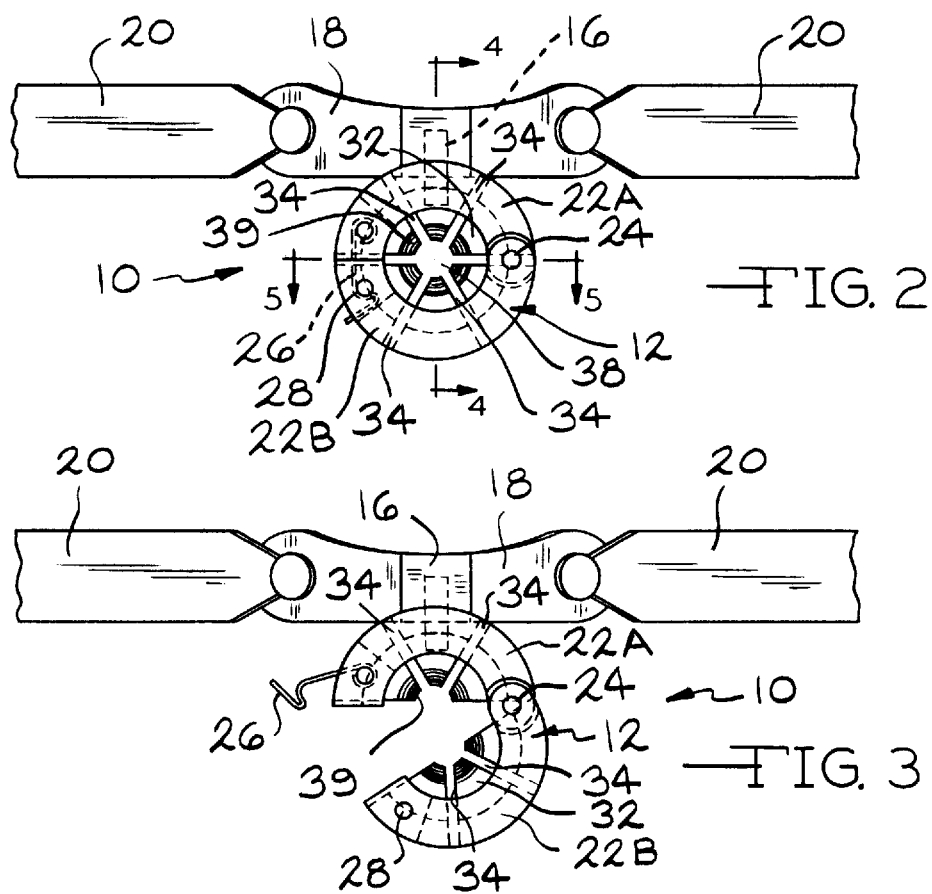
FIG. 2
FIG. 3

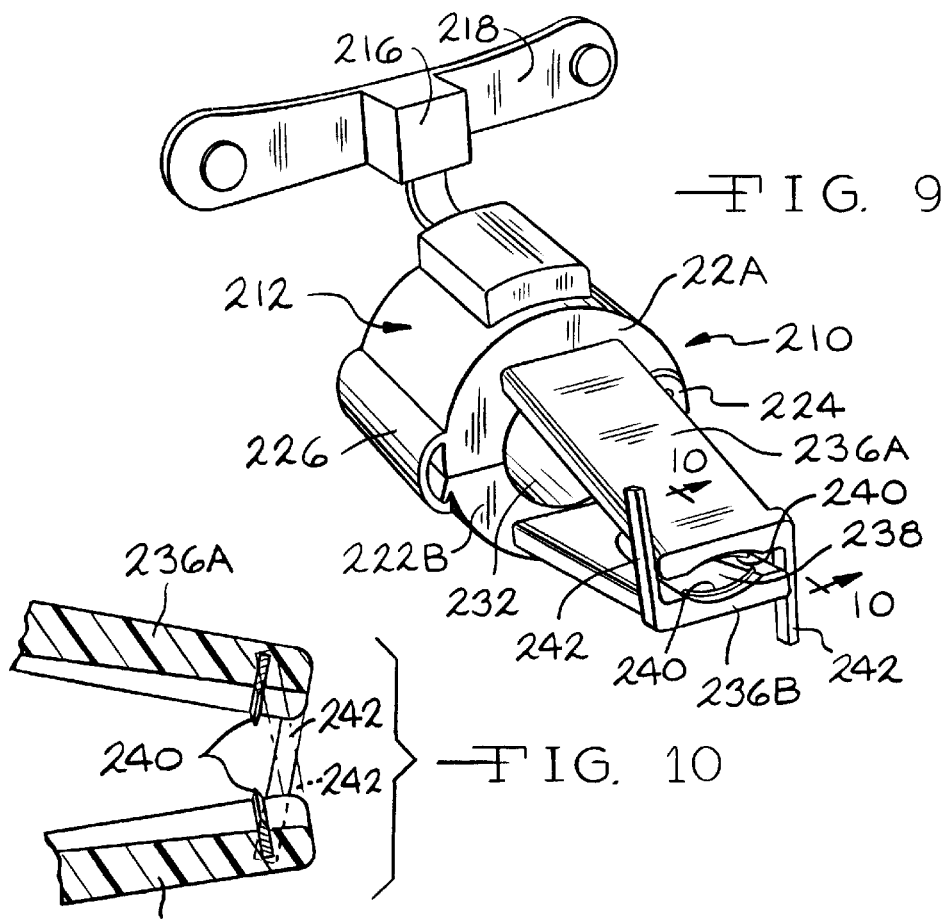
FIG. 9
FIG. 10
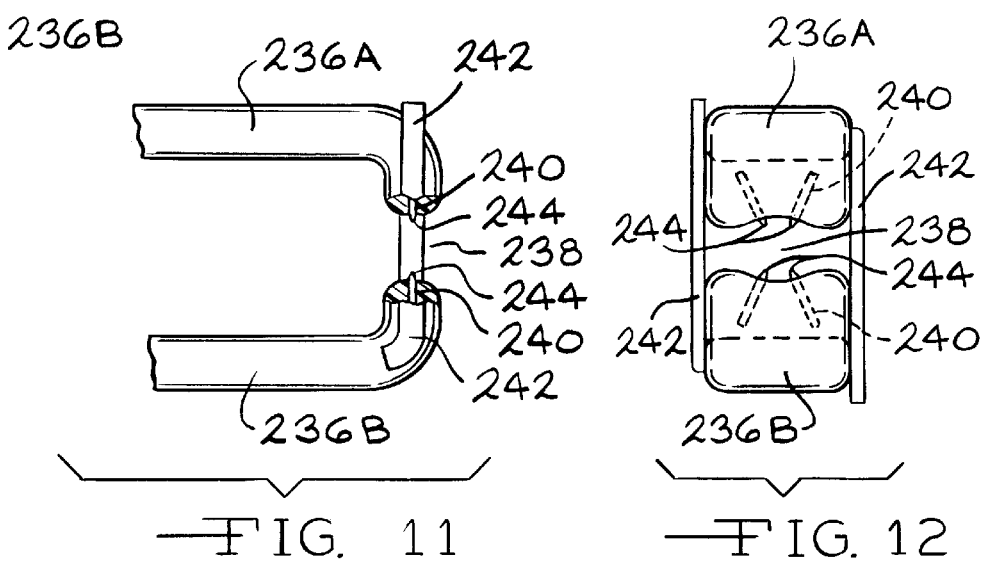
FIG. 11
FIG. 12

ENDOTRACHEAL TUBE POSITIONER

This is a divisional of application Ser. No. 08/273,409, filed on Jul. 11, 1994, now U.S. Pat. No. 5,555,881.

BACKGROUND OF THE INVENTION

The present invention relates to a medical device designed to grip and position an endotracheal tube which has been placed, either orally or nasally, into the trachea of a patient for the purpose of conveying gas to the lungs of the patient. Once the tube is correctly positioned within the patient, it is important that the tube be retained in its specified position against forces such as those occurring as a result of patient swallowing and muscular reflexes without need for removal or repositioning. The most conventional past practice for securing an endotracheal tube in a desired position is to wrap the tube with adhesive tape and secure the tape to the patient's jaws and cheeks. This manner of securing the endotracheal tube in position is quite undesirable and usually impractical, creating a large amount of patient discomfort.

Recognizing the insufficiencies of taping, there have been proposed in the prior art many varieties of endotracheal tube holders all intended to improve upon the commonplace use of tape. However, such devices have many times introduced other disadvantages and impracticalities. For instance, many of the tube holders create discomfort to the patient due to a lack of flexibility, create potentials for occlusions of the tube, and provide difficulty in adjusting and repositioning the tube as well as in maintaining a secure grip upon the tube since the tubes can be provided in a variety of diameters. Examples of such prior art are shown in U.S. Pat. Nos. 4,249,529, 4,351,331, 4,774,944, and 5,069,206.

Many commercial endotracheal tube holders also encounter problems when loading and unloading the tube. If the tube must be slid through the holder, difficulties arise due to adaptors which may need to be removed, as well as the need to slide the holder onto the tube from an unobstructed end of the tube. Many times these seemingly simple adaptions of the tube to the holder create complexities and time delays that are undesirable during medical treatment.

SUMMARY OF THE INVENTION

The general purpose of the present invention is the provision of an endotracheal tube positioner which is adaptable to properly grip, without occlusion, and maintain the position of an endotracheal tube of any shape and size. It is commonly known that endotracheal tubes are usually circular in cross section and are provided in a wide variety of diameters in an effort to facilitate the appropriate function and comfort with patients of differing sizes. Therefore, it is important to have a tube holder or positioner which is readily adaptable to easily grasp and retain the tube without pinching or occluding the tube. Furthermore, the tube positioner of the present invention is designed to be spaced apart from the patient's lips and mouth, carried by a comfortable lip bumper, thereby reducing the potential for irritation to the patient. The tube holder of this invention is commonly provided with at least two parts connected by a hinge and latch design which enables the tube to be side mounted into the tube holder or positioner.

Therefore, it is an object of this invention to provide an endotracheal tube positioner which effectively grips tubes of varying diameter without slippage and without creating an occlusion of the tube.

Another object of the invention is to provide an endotracheal tube holder adaptable for use with any patient.

Yet another object of the present invention is to provide an endotracheal tube holder which is easily operated to latch and unlatch during installation or when removal is required.

A further object of the invention is to provide an endotracheal tube positioner which is side loaded.

Other objects of the present invention will become apparent upon reading the following specification and referring to the accompanying drawings. The invention accordingly consists in features of construction, combination of elements, and arrangement of parts, which will be exemplified in the construction hereinafter described and of which the scope will be indicated by the appended claims.

BRIEF DESCRIPTION OF THE DRAWINGS

FIG. 1 is a diagrammatic view showing the endotracheal tube positioner of the present invention in use with a patient;

FIG. 2 is a front view of the endotracheal tube positioner of the present invention;

FIG. 3 is a front view of the endotracheal tube positioner of FIG. 2 in an unclasped position;

FIG. 9 is a perspective view of a second alternative embodiment of the endotracheal tube positioner;

FIG. 10 is a sectional view of the endotracheal tube positioner of FIG. 9 taken along line 10—10;

FIG. 11 is a partial side view of an alternative embodiment of the tube gripping members intended for use with the endotracheal tube positioner of FIG. 9;

FIG. 12 is a front view of the alternative embodiment of the tube gripping members of FIG. 11;

DETAILED DESCRIPTION OF THE PREFERRED EMBODIMENT

Figure 4:
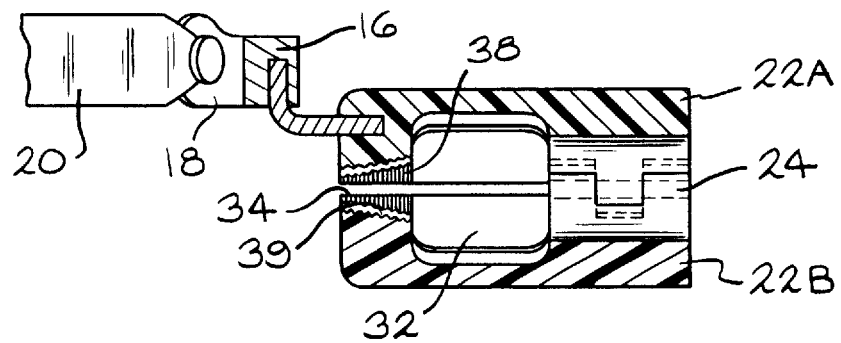
FIG. 4 is a sectional view of the endotracheal tube positioner taken along line 4—4 of FIG. 2.
Figure 5:
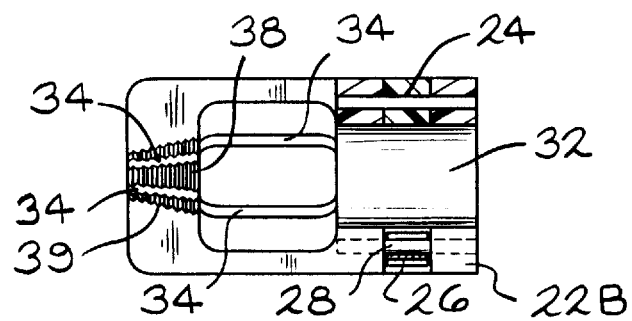
FIG. 5 is a sectional view of the endotracheal tube positioner taken along line 5—5 of FIG. 2.

The endotracheal tube positioner of the present invention is intended for use in retaining an endotracheal tube in position within a patient where the tube has been inserted, either orally or nasally. Referring to FIG. 1, the tube positioner 10 generally comprises a collar 12 engaged by means of a support member 16 with a lip bumper 18 which is designed to comfortably rest on the patient's upper or lower lip. The lip bumper 18 is held in place by straps 20 which preferably are of the loop and hook fastener variety such as that commonly marketed under the trademark VEL-CRO®.

Referring now to FIGS. 2–5 the preferred embodiment of the endotracheal tube positioner 10 is shown in detail. The tube positioner 10 is composed of a collar 12 retained by a support member 16 in engagement with a lip bumper 18. The lip bumper 18 is preferably padded or formed from a softened material to provide comfort in engagement with the patient's lip. Attached to the lip bumper 18 are straps 20 having a loop and hook design, such as that commonly marketed under the trademark VELCRO®. The collar 12 of the tube positioner 10 includes an outer body which is preferably separated into two halves 22A, 22B. The halves of the body 22A, 22B are engaged together on one side by means of a hinge member 24 preferably molded or formed from the body material, which is preferably a hardened plastic. The body halves 22A, 22B rotate about the hinge member 24 as shown in FIG. 3. While the hinge member 24 disclosed in FIGS. 2–5 is shown to be a standard rotating hinge engaged by a central pin member, it may be desirable or preferable to create the hinge member 24 as a living hinge. A clasp member 26 such as a metal hook is positioned to engage a pin 28 and close the body halves 22A, 22B together to form the collar 12 as shown in FIG. 2. The collar member 12 defines a central orifice 32 which extends axially through the collar member 12. As shown in FIGS. 2–5 the hinge 24 and clasp 26 are oriented to be proximate one end of the collar 12 and the opposed end of the collar 12 is provided with slots 34 which allow the body halves 22A, 22B to separate and radially expand and contract to accommodate endotracheal tubing of differing diameters. The same opposed end of the collar 12 includes a clamping orifice 38 axially aligned with the central orifice 32. As clearly shown in FIGS. 4 and 5, the clamping orifice 38 progressively narrows in diameter in the axial direction and is provided with grooves or knurls 39 designed to assist in gripping the smooth surface of the endotracheal tube, thereby preventing movement of the tube once it is gripped by the clamping orifice 38. The slots 34 will provide the flexibility for the body halves 22A, 22B to radially expand about the endotracheal tube as the tube is retained in the clamping orifice 38 to prevent deleterious squeezing or the occlusion of the tube upon closure of the body halves 22A, 22B about the tube. Thus, the tube positioner 10 can be used to accommodate endotracheal tubes of differing diameters.

Figure 6:
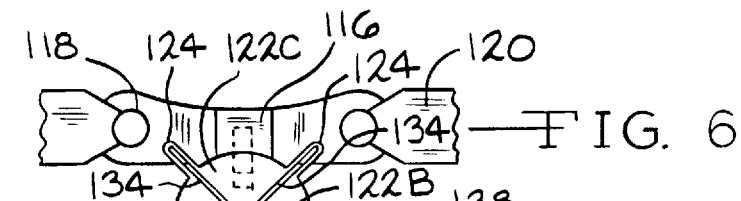
FIG. 6 is a front view of a first alternative embodiment of the endotracheal tube positioner.
Figure 7:
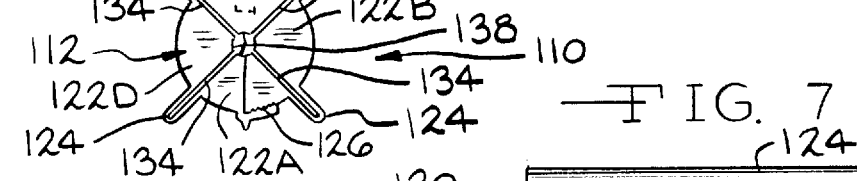
FIG. 7 is a bottom view of the endotracheal tube positioner of FIG. 6.
Figure 8:
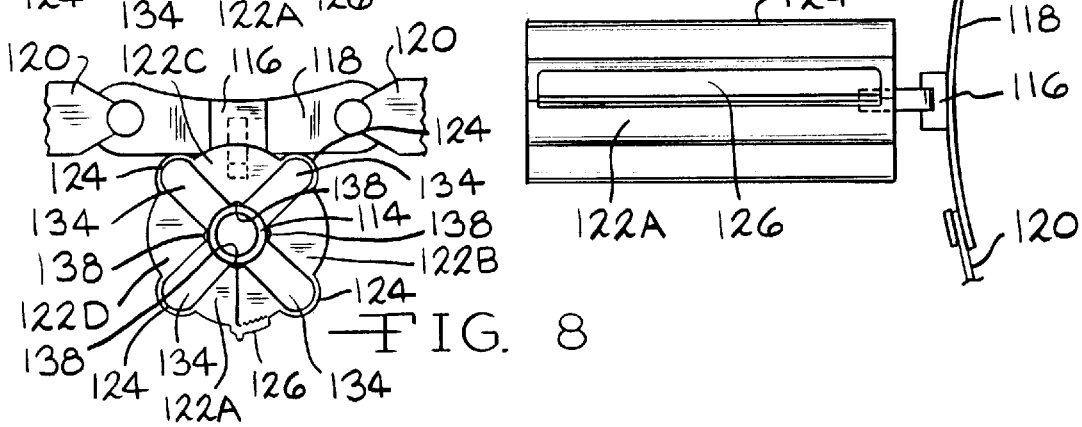
FIG. 8 is a front view showing the endotracheal tube positioner of FIG. 6 in an expanded position about an endotracheal tube.
Figure 13:
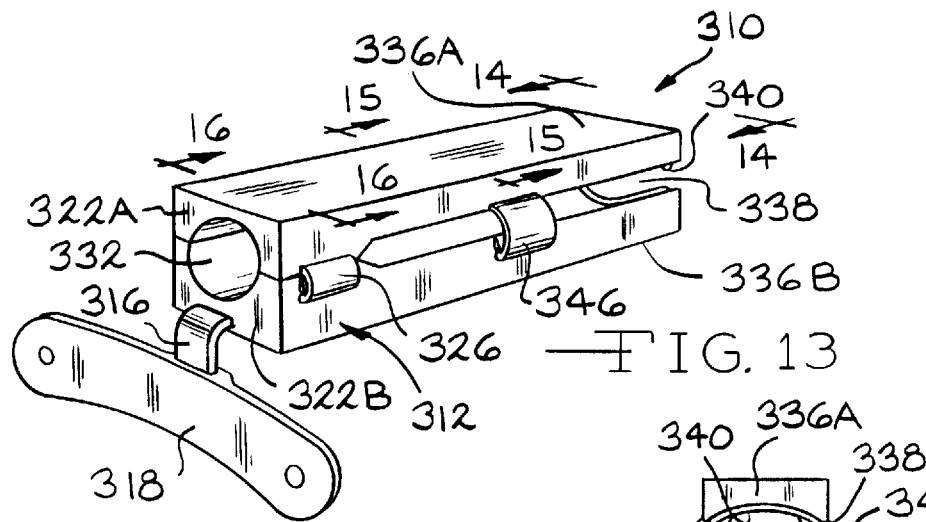
FIG. 13 is a perspective view of a third alternative embodiment of the endotracheal tube positioner of the present invention.
Figure 14:
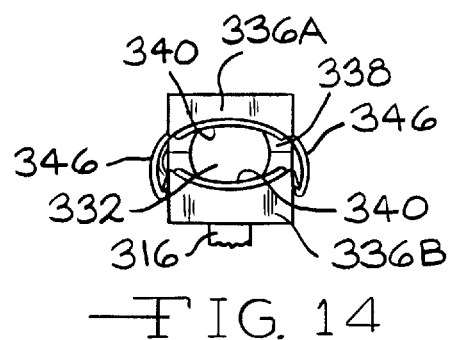
FIG. 14 is a sectional view of the endotracheal tube positioner taken along line 14—14 of FIG. 13.
Figure 15:
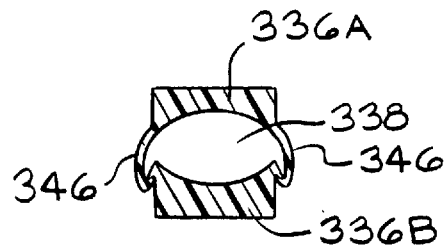
FIG. 15 is a sectional view of the endotracheal tube positioner taken along line 15—15 of FIG. 13.
Figure 16:
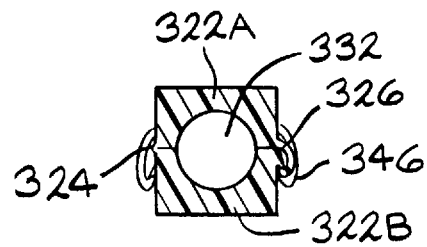
FIG. 16 is a sectional view of the endotracheal tube positioner taken along line 16—16 of FIG. 13.

Referring now to FIGS. 6–8, an alternative embodiment of the tube positioner 110 is shown. The tube positioner 110 includes a collar member 112 engaged by means of a support member 116 to a lip bumper 118. Straps 120 having a hook and loop configuration, such as the product marketed under the trademark VELCRO® are engaged with the lip bumper 118 to secure the tube positioner 110 in an appropriate position with respect to the patient's oral or nasal cavities. The straps 120 and the lip bumper 118 are of the same design as that described earlier with regard to the preferred embodiment. The collar member 112 includes a body quartered into equal sections 122A, 122B, 122C, 122D, separated by slots 134. One section 122A is further divided to allow the body to be opened to accept the insertion of an endotracheal tube. The four body sections 122A–D are engaged with each other by means of living hinges 124 positioned about the slots 134 located between the body sections 122A–D. A clasp member 126 is positioned across the split body section 122A to provide a locking mechanism as the body is enclosed about the endotracheal tube 114. Referring to FIG. 8, the tube positioner 110 of the first alternative embodiment is shown retaining an endotracheal tube 114 in position. The body portions 122A–D have expanded radially outward to accept the endotracheal tube 114. The endotracheal tube 114 is held into position by contact with the interior surface 138 of the body sections 122A–D as the sections expand radially about their living hinges 124 and slots 134.

Referring now to FIGS. 9–12, a second alternative embodiment of the tube positioner 210 is shown having a collar 212 engaged by means of a support member 216 to a lip bumper 218. The lip bumper 218 is similar to that described earlier with respect to the preferred embodiment and is designed to be utilized with straps (not shown) similar to those described earlier with regard to the preferred embodiment. The collar 212 is composed of a body member having two half sections 222A, 222B engaged about a hinge member 224 with a clasp or snap member 226 designed to hold the two halves 222A, 222B together. Preferably the hinge member 224 is a living hinge formed of the same material as the collar 212. The body sections 222A, 222B engage together to define a central orifice 232 which extends axially therethrough. Tube retaining fingers 236 extend from the body sections 222A, B, a first retaining finger 236A extending from the body section 222A and a second retaining finger 236B extending from the body section 222B. The retaining fingers 236A, B Converge toward each other to create a narrow clamping orifice 238 which is axially aligned with the central orifice 232 of the body 222. The retaining fingers 236A, B are each provided with a sharp ridge 240 in opposed relationship, the ridges 240 being intended to engage and retain the endotracheal tube without creating occlusions within the tube. The retaining fingers 236A, B are preferably formed of a material which allows for resilient expansion or radial deflection about the clamping orifice 238 to accommodate tubes of differing diameters. The side bars 242 positioned at each end of the retaining fingers 236A, B are intended to prevent the endotracheal tube from slipping sideways out of the clamping orifice 238.

Referring now to FIGS. 11 and 12, an alternative embodiment of the retaining fingers 236 intended for use with the tube holder 210 of FIG. 9 Is shown wherein the retaining fingers 236 are curved at their ends to provide an inline vertical relationship between the gripping points 240 located on each retaining finger 236A, 236B. The retaining fingers 236A, B further include the side restraint members 242 as previously described. The gripping points 240 are defined by four angularly disposed pikes 244 which are positioned about the curved clamping orifice 238 created by the retaining fingers 236A, B.

Figure 17:
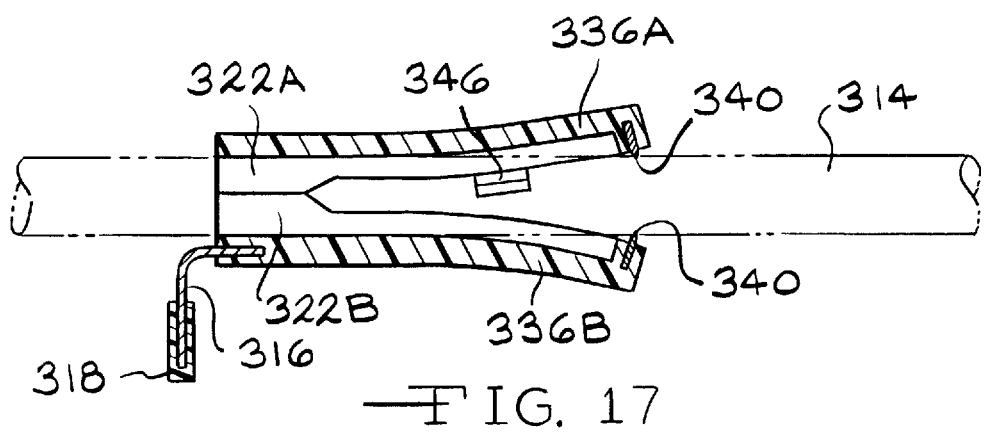
FIG. 17 is a sectional view of the endotracheal tube positioner showing an endotracheal tube retained in position.

Referring now to FIGS. 13–17, a third alternative embodiment of the tube positioner 310 of the present invention is shown in detail. The tube positioner 310 includes a collar member 312 which is engaged by means of a support member 316 to a lip bumper 318. The lip bumper 318 is intended to be used with strap members (not shown) and the lip bumper 318 and strap members are similar to those described previously with regard to the preferred embodiment. The collar member 312 includes body portions 322A, 322B which are engaged together on one side by a hinge member 324, preferably a living hinge and define a central orifice 332 extending axially therethrough. The body portions are fixed together by a clasp member 326 located on the side opposed to the hinge member 324. The body portions 322A, B Include retaining fingers 336A, B which extend from the body members 322A, B to form a clamping orifice 338 axially aligned with the central orifice 332. The retaining fingers 336A, B are engaged on each side by a clamping clasp or snap member 346 which holds the retaining fingers in position about an endotracheal tube of small diameter. The retaining fingers 336A, 336B further include a ridge 340 of gripping members designed to engage and hold the endotracheal tube in position without occluding the tube. The retaining fingers 336A, B are radially deflective as shown in FIG. 17 to expand and contract In order to accommodate tubing of differing diameters.

The above descriptions of the structures relating to the preferred embodiment and three alternative embodiments are intended to be instructive and are not intended to be fully limiting upon the scope of the following claims.

We claim:

1. An endotracheal tube holder for use in retaining an endotracheal tube in a desired position comprising in combination: a collar member formed from at least two body portions engaged together to define an axially oriented orifice extending therethrough, said body portions being joined together by at least one hinge member and at least one catch member; at least two tube clamping members, each of which is respectively engaged with one of said body members, said clamping members deflectively engaging the endotracheal tube as such tube is positioned in said orifice; and a strap member for securing said tube holder in such desired position.

2. The tube holder of claim 1, wherein said body portions are separated by radially oriented slots and are engaged to each other by living hinges located at the outermost radial extreme of said slots whereby said body portions radially expand about said slots and said living hinges to accommodate and grasp such tube.

3. The tube positioner of claim 1, wherein said clamping members include radially deflective retaining fingers, each of said retaining fingers engaged with one of said body portions, said retaining fingers being oriented to extend radially inward toward each other to form a clamping orifice spaced from said body portions and axially aligned with said central orifice; and a sharpened protrusion extending from the distal end of such of said retaining fingers to engage and retain such tube in said clamping orifice.

4. The tube positioner of claim 1, wherein said clamping members include radially deflective retaining fingers, each of said retaining fingers engaged with one of said body portions and extending axially therefrom, the distal ends of said retaining fingers forming a clamping orifice spaced from said body portions and axially aligned with said central orifice, and sharpened protrusions extending from the distal end of each of said retaining fingers to engage and retain said tube in said clamping orifice.

* * * * *